US009580682B1

(12) United States Patent
Kim et al.

(10) Patent No.: US 9,580,682 B1
(45) Date of Patent: Feb. 28, 2017

(54) METHOD FOR INDUCING ENDODERMAL AND MESODERMAL DIFFERENTIATION FROM HUMAN PLURIPOTENT STEM CELLS BY CXCR2 SUPPRESSION

(71) Applicant: KOREA UNIVERSITY RESEARCH AND BUSINESS FOUNDATION, Seoul (KR)

(72) Inventors: Byung Soo Kim, Seoul (KR); Ji-Hye Jung, Seoul (KR); Yong Park, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 14/936,774

(22) Filed: Nov. 10, 2015

(30) Foreign Application Priority Data

Aug. 12, 2015 (KR) ........................ 10-2015-0113834

(51) Int. Cl.
*C12N 5/00* (2006.01)
*C12N 5/073* (2010.01)

(52) U.S. Cl.
CPC .... *C12N 5/0605* (2013.01); *C12N 2501/2308* (2013.01); *C12N 2506/03* (2013.01)

(58) Field of Classification Search
CPC .......... C12N 5/0605; C12N 2501/2308; C12N 2506/03
See application file for complete search history.

(56) References Cited

U.S. PATENT DOCUMENTS

2003/0153082 A1    8/2003  Bhatia

FOREIGN PATENT DOCUMENTS

WO          03040319 A2    5/2003

OTHER PUBLICATIONS

Jung et al. 24(8):948-961. Pub date:Apr. 15, 2015; electronic pub date Dec. 23, 2014.*
Bento et al. J. Leukoc. Biol. 84:1213-1221, 2008.*
Bradley et al. Br. J. Pharm. 158:328-338, 2009.*
Cai, C., et al., "Directing the differentiation of embryonic stem cells to neural stem cells", "Developmental Dynamics", Dec. 2007, pp. 3255-3266, vol. 236.
D'Amour, K., et al., "Efficient differentiation of human embryonic stem cells to definitive endoderm", "Nature Biotechnology", Oct. 28, 2005, pp. 1534-1541, vol. 23, No. 12.
Gao, R., et al., "Characterization of endocrine progenitor cells and critical factors for their differentiation in human adult pancreatic cell culture", "Diabetes", Aug. 2003, pp. 2007-2015, vol. 52.
Hori, Y., et al., "Differentiation of insulin-producing cells from human neural progenitor cells", "PLoS Medicine", Apr. 26, 2005, pp. e103 (0347-0356), vol. 2, No. 4.
Jung, J., et al., "CXCR2 and its related ligands play a novel role in supporting the pluripotency and proliferation of human pluripotent stem cells", "Stem Cells and Development", Dec. 23, 2014, pp. 948-961, vol. 24, No. 8.
Jung, J., et al., "CXCR2/MTOR/Beta-Catenin and human telomerase catalytic subunit axis supports human pluripotent stem cells", "Late Breaking Abstracts", Jun. 24-27, 2015, p. 17 (Abstract), International Society for Stem Cell Research 2015 Annual Meeting, Stockholm, Sweden.
Kaspi, H., et al., "Brief report: miR-290-295 regulate embryonic stem cell differentiation propensities by repressing Pax6", "Stem Cells", Oct. 2013, pp. 2266-2272, vol. 31.
Kubo, A., et al., "Development of definitive endoderm from embryonic stem cells in culture", "Development", Mar. 3, 2004, pp. 1651-1662, vol. 131.
Nakajima-Nagata, N., et al., "In vitro induction of adult hepatic progenitor cells into insulin-producing cells", "Biochemical and Biophysical Research Communications", Jun. 4, 2004, pp. 625-630, vol. 318.
Noisa, R, et al., "Identification and Characterisation of the Early Differentiating Cells in Neural Differentiation of Human Embryonic Stem Cells", "PLoS One", May 15, 2012, pp. e37129 (1-11), vol. 7, No. 5.
Tada, S., et al., "Characterization of mesendoderm: a diverging point of the definitive endoderm and mesoderm in embryonic stem cell differentiation culture", "Development", Sep. 1, 2005, pp. 4363-4374, vol. 132.
Takahashi, T., et al., "Ascorbic acid enhances differentiation of embryonic stem cells into cardiac myocytes", "Circulation", Mar. 31, 2003, pp. 1912-1916, vol. 107.
Teo, A., et al., "Pluripotency factors regulate definitive endoderm specification through eomesodermin", "Genes & Development", Jan. 18, 2011, pp. 238-250, vol. 25.
Verfaille, C., "Stem cell plasticity", "Hematology", Feb. 2005, pp. 293-296, vol. 10 Suppl 1.

(Continued)

*Primary Examiner* — Marcia S Noble
(74) *Attorney, Agent, or Firm* — Hultquist, PLLC; Steven J. Hultquist

(57) ABSTRACT

The present invention relates to a method of inducing the differentiation of human pluripotent stem cells into endoderm and mesoderm by CXCR2 inhibition, and more particularly, to a method of promoting the differentiation of human pluripotent stem cells into endoderm and mesoderm by inhibiting the expression of the surface receptor CXCR2 in the stem cells by use of an shRNA technique. The method of inducing the differentiation of human pluripotent stem cells into endoderm or mesoderm by CXCR2 inhibition according to the present invention can increase the efficiency and utility of stem cells as a cell therapeutic agent, because it promotes the differentiation of stem cells into a specific germ layer serving as the origin of target cells, which is the first important step for inducing the differentiation of stem cells into specific cells.

7 Claims, 5 Drawing Sheets

(56) References Cited

OTHER PUBLICATIONS

Yang, C., et al., "A key role for telomerase reverse transcriptase unit in modulating human embryonic stem cell proliferation, cell cycle dynamics, and in vitro differentiation", "Stem Cells", Jan. 17, 2008, pp. 850-863, vol. 26.

Yasunaga, M., et al., "Induction and monitoring of definitive and visceral endoderm differentiation of mouse ES cells", "Nature Biotechnology", Nov. 27, 2005, pp. 1542-1550, vol. 23, No. 12.

Zalzman, M., et al., "Reversal of hyperglycemia in mice by using human expandable insulin-producing cells differentiated from fetal liver progenitor cells", "PNAS", May 19, 2003, pp. 7253-7258, vol. 100, No. 12.

Zhou, J., et al., "mTOR supports long-term self-renewal and suppresses mesoderm and endoderm activities of human embryonic stem cells", "PNAS", May 12, 2009, pp. 7840-7845, vol. 106, No. 19.

\* cited by examiner

FIG. 1
FIG. 1C
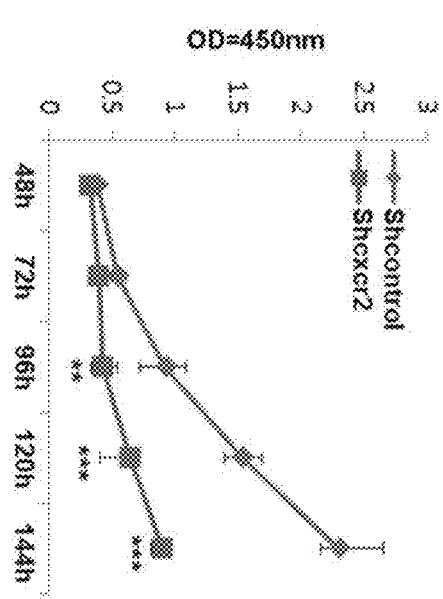
FIG. 1A
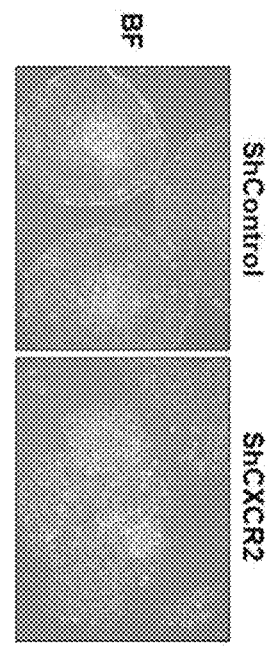
FIG. 1B
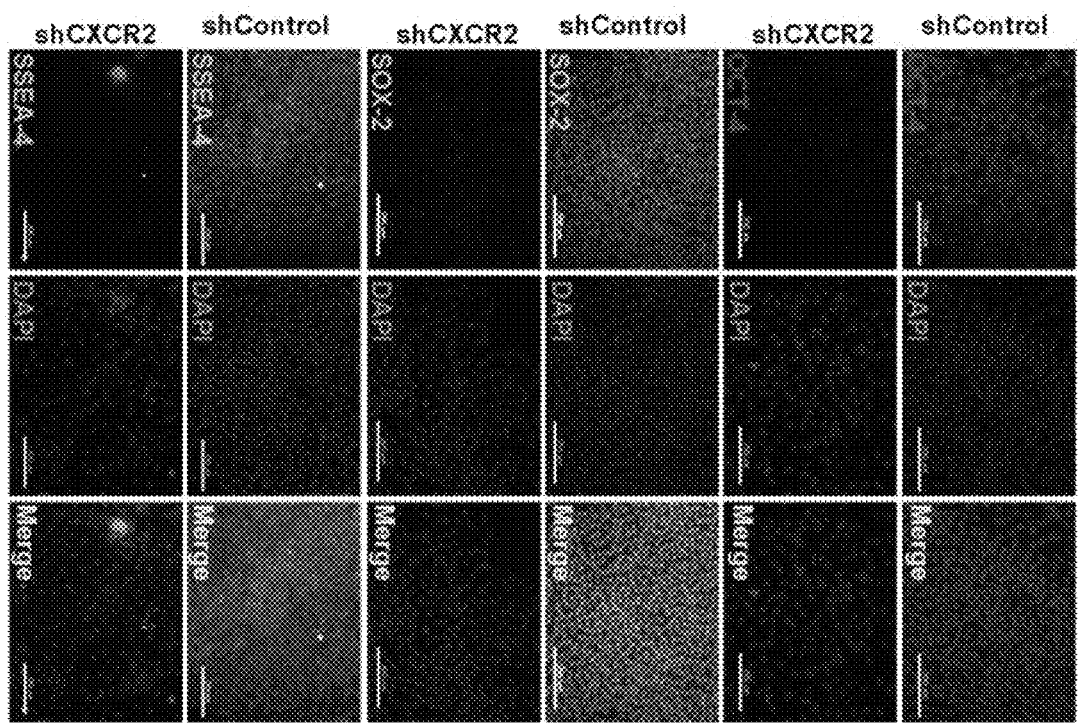

METHOD FOR INDUCING ENDODERMAL AND MESODERMAL DIFFERENTIATION FROM HUMAN PLURIPOTENT STEM CELLS BY CXCR2 SUPPRESSION

CROSS-REFERENCE TO RELATED APPLICATION

The priority of Korean Patent Application No. 10-2015-0113834 filed Aug. 12, 2015 is hereby claimed under the provisions of 35 USC 119. The disclosure of Korean Patent Application no. 10-2015-0113834 is hereby incorporated herein by reference, in its entirety, for all purposes.

TECHNICAL FIELD

The present invention relates to a method of inducing the differentiation of human pluripotent stem cells into endoderm and mesoderm by CXCR2 inhibition, and more particularly, to a method of promoting the differentiation of human pluripotent stem cells into endoderm and mesoderm by inhibiting the expression of the surface receptor CXCR2 in the stem cells by use of an shRNA technique.

BACKGROUND ART

Stem cells refer to cells having not only self-replicating ability but also the ability to differentiate into at least two types of cells, and can be divided into totipotent stem cells, pluripotent stem cells, and multipotent stem cells. In recent years, studies have been actively conducted to treat various diseases with stem cells capable of differentiating into various cells. Thus, the ultimate object of stem cell studies is to make a desired type of cell or tissue for use in technology such as cell therapy or tissue engineering.

Thus, the problem to be solved to use stem cells in actual applications is the development of a technology capable of inducing the differentiation of stem cells into desired cells. Accordingly, studies have been attempted to induce stem cells to differentiate into specific cells, and induced pluripotent stem (iPS) cells produced by reprogramming of somatic cells, etc., have been used in cell differentiation.

Generally, methods of promotes differentiation are used to induce the differentiation of stem cells. Typical examples of these methods include a method of inducing the differentiation of embryonic stem cells into neurons by using retionic acid (*Dev. Dyn.* 236:3255-3266, 2007), a method of inducing the differentiation of embryonic stem cells into hepatocytes by using activin A (*Nat. Biotechnol.* 23:1534-1541, 2005), a method of inducing the differentiation of embryonic stem cells into cardiomyocytes by using ascorbic acid (*Circulation* 107:1912-1916, 2003), and the like. However, conventional methods have disadvantages in that these methods are expensive due to the use of expensive reagents such as cytokines and show low differentiation rates. Thus, in order to effectively use stem cells in various fields, it is required to develop an inexpensive and easy method capable of inducing the differentiation of stem cells into a desired specific tissue with high differentiation efficiency.

In most vertebrates including humans, three-germ-layer cells (endoderm, mesoderm and ectoderm) are formed through gastrulation of early embryos, and all cells constituting the human body tissue differentiate from the three-germ-layer cells. In the case of embryonic stem cells established in vitro by extracting an inner cell mass from blastocysts that are early embryos, an event similar to gastrulation is observed during the formation of embryoid bodies. The first important step for inducing the differentiation of specific cells from embryonic stem cells is to increase a specific germ layer which is the origin of the target cells to be obtained by differentiation, and inducing the differentiation of desired cells from the three-germ-layer cells will be the most efficient differentiation method. In particular, in order to increase the utility of stem cells as a cell therapeutic agent, a technique of efficiently inducing the differentiation of stem cells into specific cells is required.

In recent years, a method of promoting the differentiation of human pluripotent stem cell-derived embryoid bodies by inhibiting their mTOR (mammalian target of rapamycin) (Zhou J et al., *Proc Natl Acad Sci USA.* 106(19):7840-5, 2009), and a method of promoting the differentiation of human pluripotent stem cells by inhibiting their telomerase (Yang C et al., *Stem Cells.* 26(4):850-63, 2008), have been reported. However, the method of inhibiting mTOR is a technique that does not act on a cell receptor, but acts on a signaling protein, and the method of inhibiting telomerase is also a technique that does not act on a cell receptor, but acts on the telomere-maintenance enzyme telomerase. In this method, non-specific differentiation into any other cell type, including endoderm, mesoderm and ectoderm, is promoted. In order to control the differentiation of human pluripotent stem cell-derived embryoid bodies, it is most important to develop a technique that acts on a cell receptor. This is because a technique that acts on a signaling protein or enzyme is highly likely influenced by other intracellular factors that influence signaling or enzymatic activity, compared to a technique that acts on a cell receptor, and because an operation for controlling the degree of differentiation can be relatively difficult. However, controlling the differentiation of human pluripotent stem cell-derived embryoid bodies by use of a cell receptor is not yet known.

Accordingly, the present inventors have made extensive efforts to induce the differentiation of stem cells into desired specific tissue or cells in order to increase the utility of stem cells as a cell therapeutic agent, and as a result, have found that the selective differentiation of human pluripotent stem cells into endoderm and mesoderm is promoted by inhibiting the expression of a CXCR2 receptor, thereby completing the present invention.

DISCLOSURE OF INVENTION

It is an object of the present invention to provide a method for inducing the differentiation of pluripotent stem cells into endoderm or mesoderm, the method comprising a step of either treating the pluripotent stem cells with a CXCR2 expression inhibitor or culturing the pluripotent stem cells in a medium containing a CXCR2 antagonist.

Another object of the present invention is to provide a composition for inducing the differentiation of pluripotent stem cells into endoderm or mesoderm, the composition containing a CXCR2 antagonist as an active ingredient.

To achieve the above objects, the present invention provides a method for inducing the differentiation of pluripotent stem cells into endoderm or mesoderm, the method comprising a step of either treating the pluripotent stem cells with a CXCR2 expression inhibitor or culturing the pluripotent stem cells in a medium containing a CXCR2 antagonist.

The present invention also provides a composition for inducing the differentiation of pluripotent stem cells into endoderm or mesoderm, the composition containing a CXCR2 antagonist as an active ingredient.

ADVANTAGEOUS EFFECTS

The method of inducing the differentiation of human pluripotent stem cells into endoderm or mesoderm by CXCR2 inhibition according to the present invention can increase the efficiency and utility of stem cells as a cell therapeutic agent, because it promotes the differentiation of stem cells into a specific germ layer serving as the origin of target cells, which is the first important step for inducing the differentiation of stem cells into specific cells.

BRIEF DESCRIPTION OF THE DRAWINGS

FIG. 1(A) is a 40× magnification image showing human pluripotent stem cells after inhibiting the expression of the CXCR2 gene using shRNA; FIG. 1(B) shows the results of analyzing the expression of human pluripotent stem cell marker genes (OCT4, SOX2 and SSEA-4) by immunofluorescence staining after inhibition of CXCR2 gene expression; and FIG. 1(C) shows the results of analyzing the proliferation of human pluripotent stem cells after inhibition of CXCR2 gene expression.

BEST MODE FOR CARRYING OUT THE INVENTION

Figure 2:
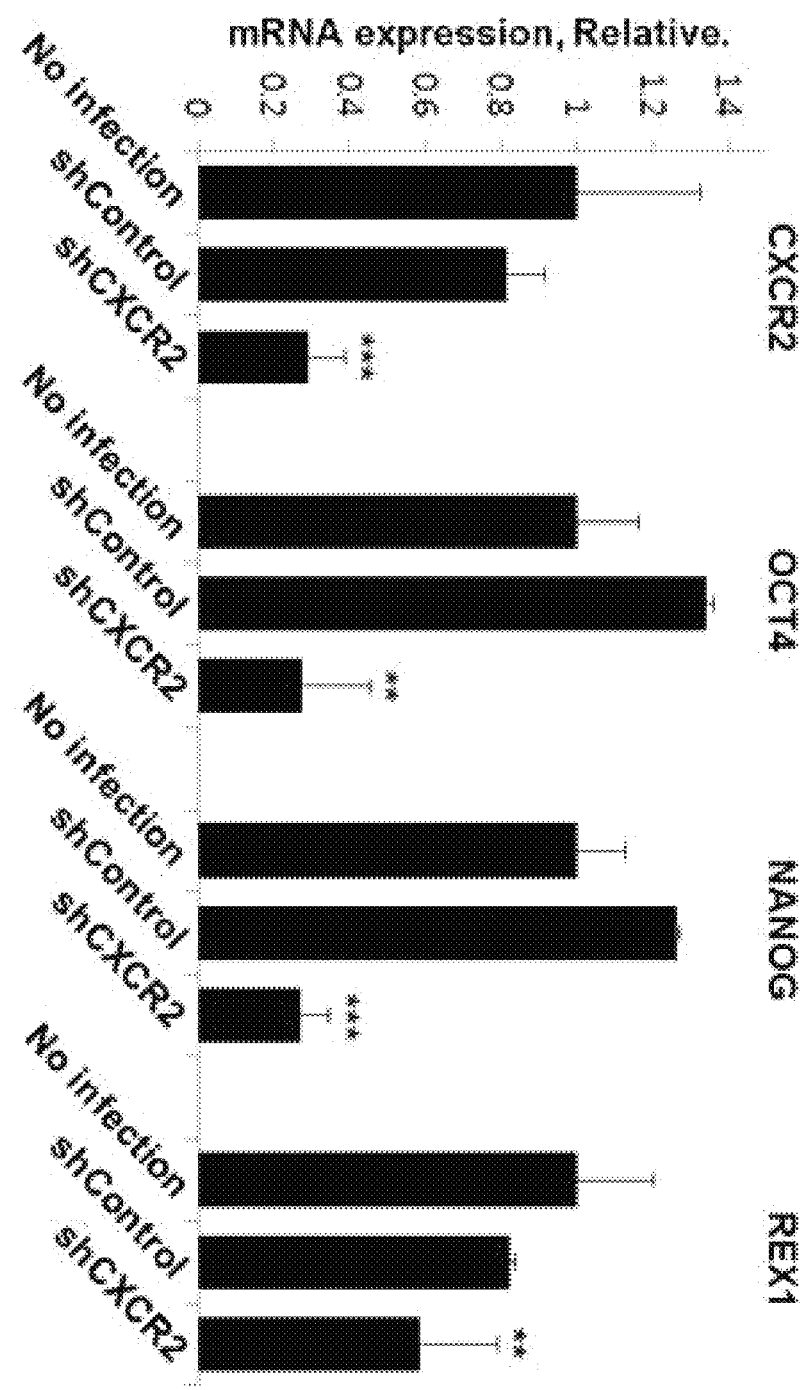
FIG. 2 shows the results of analyzing the expression of human pluripotent stem cell marker genes (OCT4, NANOG and REX-1) by real-time quantitative PCR after inhibition of CXCR2 gene expression.
Figure 3:
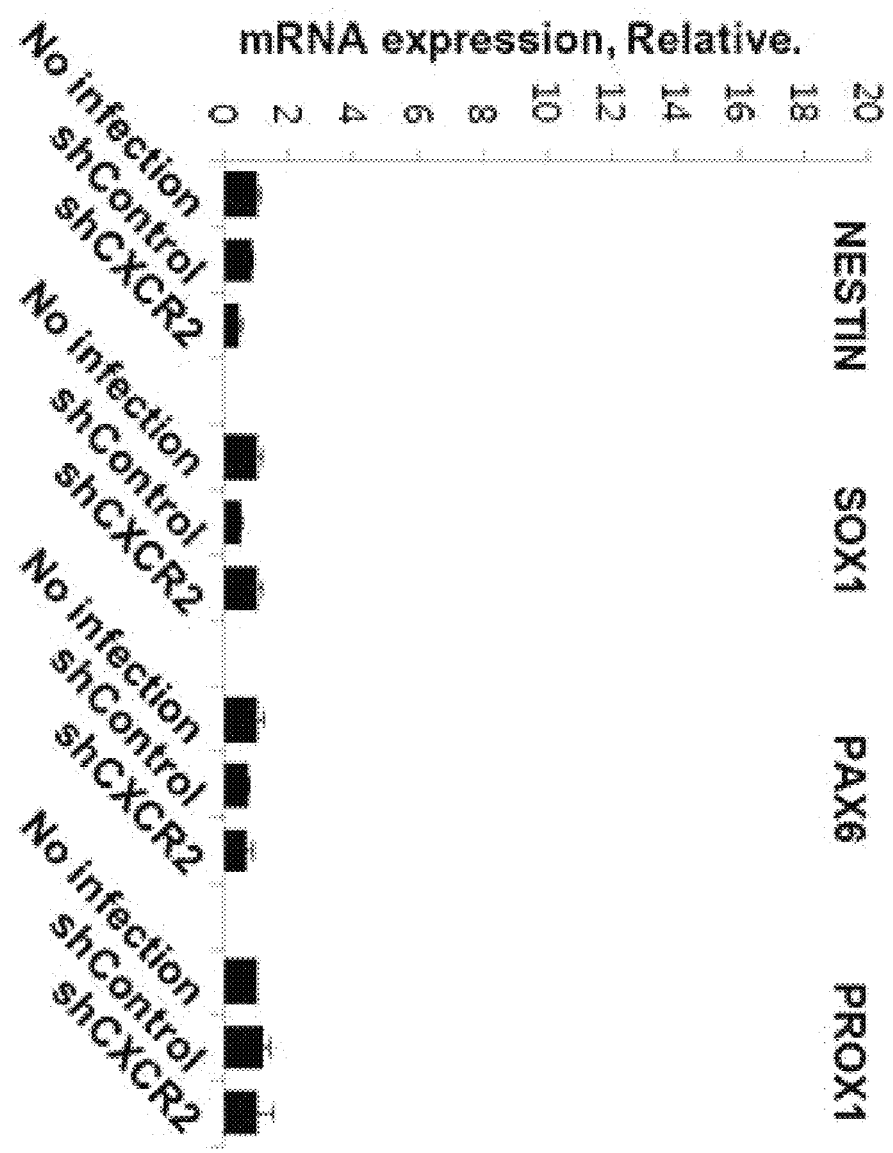
FIG. 3 shows the results of analyzing the expression of ectodermal genes, including Nestin, Sox1, Pax6 and Prox1, by real-time quantitative PCR.

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

In the present invention, human pluripotent stem cells were treated with an shRNA specific for the mRNA of the surface receptor CXCR2 to thereby inhibit the expression of the CXCR2 gene, and then the expressions of endoderm-specific genes, including AFP, GATA4, ZO1, SOX17 and CXCR4, and mesoderm-specific genes, including T, Snail2, Myocardin, twist1 and mixl1, were analyzed by real-time quantitative PCR. As a result, it was shown that the differentiation of human pluripotent stem cells into endoderm and mesoderm was markedly induced by inhibition of CXCR2.

Thus, in one aspect, the present invention is directed to a method for inducing the differentiation of pluripotent stem cells into endoderm or mesoderm, the method comprising a step of either treating the pluripotent stem cells with a CXCR2 expression inhibitor or culturing the pluripotent stem cells in a medium containing a CXCR2 antagonist.

CXCR2 (CXC-chemokine receptor 2) is a receptor of conventional chemoattractant.

In the present invention, the "CXCR2 expression inhibitor" means degradation of the mRNA of the CXCR2 gene or inhibiting translation of the mRNA.

In the present invention, the CXCR2 expression inhibitor is preferably an shRNA specific for CXCR2 mRNA, and the shRNA is preferably selected from the group consisting of SEQ ID NOS: 1 to 3, but is not limited thereto.

RNA interference (RNAi) is a mechanism by which the expression of a target gene is selectively inhibited. A mediator of sequence-specific mRNA degradation is a 19-23-nucleotide small interfering RNA produced from a longer dsRNA by digestion with ribonuclease III. A cytoplasmic RISC (RNA-induced silencing complex) binds to an siRNA and directs degradation of an mRNA comprising a sequence complementary to one strand of the siRNA. The application of RNA interference in mammals has a therapeutic gene silencing effect. Despite the advantages of an siRNA, the clinical application of the siRNA is limited in that the siRNA should be prepared in vitro and a knockdown gene should be delivered by transient transfection for generally 6-10 days. Such disadvantages can be overcome by an shRNA (small-hairpin RNA) system of the present invention.

In the present invention, the shRNA for inhibiting CXCR2 expression has a sequence complementary to a portion of the CXCR2 gene, and can degrade the mRNA of the CXCR2 gene or inhibit translation of the mRNA. Specific examples of the shRNA according to the present invention include the following sequences:

```
SEQ ID NO: 1:
GTCTACTCATCCAATGTTATTCAAGAGATAACATTGGATGAGTAGAC

SEQ ID NO: 2:
CCTCAAGATTCTAGCTATATTCAAGAGATATAGCTAGAATCTTGAGG

SEQ ID NO: 3:
GCCACTAAATTGACACTTATTCAAGAGATAAGTGTCAATTTAGTGGC
```

A substance that inhibits CXCR2 expression via RNAi may be artificially and chemically synthesized. The substance can also be prepared through in vitro RNA synthesis using a DNA having a hairpin structure wherein a sense strand DNA sequence and an antisense strand DNA sequence are linked in a reverse manner and T7 RNA polymerase. In the case of in vitro synthesis, antisense and sense RNAs can be synthesized from a template DNA using T7 RNA polymerase and T7 promoter. When these RNAs are annealed in vitro and then introduced into cells, RNAi is induced to direct degradation of CXCR2 mRNA. Introduction of the RNAs into cells may be performed using a calcium phosphate method, a method employing various transfection reagents (e.g., oligofectamine, lipofectamine and lipofection), or the like.

As a substance that inhibits CXCR2 expression via RNAi, an expression vector containing an shRNA or the DNA may be used, and cells containing this expression vector may also be used. A method for delivery of a gene such as an shRNA expression vector that inhibits CXCR2 expression is not specifically limited, as long as the shRNA or shRNA expression vector that inhibits CXCR2 expression is expressed in cells. For example, a gene can be introduced using a viral vector or a liposome. In the present invention, preferred examples of a virus (or viral vector) useful for delivery of the shRNA include lentivirus, adenovirus, retrovirus, adeno-associated virus, etc.

In another aspect, the present invention is directed to a composition for inducing the differentiation of pluripotent stem cells into endoderm or mesoderm, the composition containing a CXCR2 antagonist as an active ingredient.

In the present invention, the "CXCR2 antagonist" means to inhibiting the CXCR2 activity, and the antagonist may interfere with the binding of natural ligand and the receptor by binding to the receptor.

In the present invention, the CXCR2 antagonist is preferably SB225002 or SB265610, but is not limited thereto.

In the present invention, the endoderm preferably expresses one or more genes selected from the group consisting of AFP, GATA4, ZO1, SOX17, and CXCR4 (Kevin A D'Amour et al., nature biotech 23:1534-1541, 2005; AKK Teo et al., Genes & Development 25(3):238-250, 2011; C Verfaillie et al., Hematology 10(S1):293-296, 2005; H Kaspi et al., Stem Cells 31(10):2266-72, 2013; P Noisa et al., PLoS One 7(5); e37129, 2012), and the mesoderm preferably expresses one or more genes selected from the group consisting of T, Snail2, Myocardin, twist1, and mixl1 (Kevin A D'Amour et al., nature biotech 23:1534-1541, 2005; AKK Teo et al., Genes & Development 25(3):238-250, 2011; C Verfaillie et al., Hematology 10(S1):293-296, 2005; H Kaspi et al., Stem Cells 31(10):2266-72, 2013; P Noisa et al., PLoS One 7(5); e37129, 2012), but is not limited thereto.

Particularly, it is difficult to induce the differentiation of endoderm-derived specific cells (e.g., endoderm-derived hepatocytes or pancreatic cells), compared to mesoderm or ectoderm-derived specific cells, but cells (hepatocytes or insulin-secreting pancreatic cells) required for cell therapy for diabetes, liver cirrhosis and various intractable diseases are derived from endodermal cells. For this reason, many studies on the induction of differentiation from endodermal cells into specific cells (e.g., hepatocytes or pancreatic cells) have been conducted (Kubo et al, Development, 131:1651-1662, 2004; Tada et al, Development, 132:4363-4374, 2005; D'Amour et al, Nat. Biotechnol., 23:1534-1541, 2005; Yasunaga et al, Nat. Biotechnol., 23:1542-1550, 2006).

However, Generally, to induce stem cells to differentiate into endodermal, mesodermal or ectodermal cells, a method employing a biochemical agent that induces differentiation in a manner specific for type of endoderm, mesoderm and ectoderm is used. Specifically, in conventional methods, retinoic acid, lithium chloride, basic fibroblast growth factor (bFGF), epidermal growth factor (EGF) or the like is used for differentiation into ectodermal cells, and beta cellulin, activin, sonic hedgehog (shh) or the like is used for differentiation into endodermal cells. In addition, dexamethasone, dimethyl sulfoxide, basic fibroblast growth factor, vascular endothelial growth factor (VEGF) or the like is used for differentiation into mesodermal cells. As described above, very diverse drugs are used depending on the direction of differentiation, and various combinations of such biochemical agents for inducing differentiation may also be used. However, as mentioned above, there is a problem in that the rate of differentiation is low despite the use of various biochemical agents as described above. In addition, in most conventional differentiation methods, the viability of cells has become a big problem, because the differentiation process progresses over a long period of time and a large amount of cells die during the differentiation process. Furthermore, the conventional methods are disadvantageous in economic terms, because the above-described bFGF, FGF8, SHH, BDNF and the like are very expensive. However, the induction of differentiation into endoderm and mesoderm by CXCR2 inhibition according to the present invention is not influenced by a culture medium composition (i.e., the presence or absence of bFGF) for culturing human pluripotent stem cells.

In the present invention, the pluripotent stem cells are preferably human embryonic stem cells or human induced pluripotent stem (iPS) cells, but are not limited thereto. As used herein, the term "pluripotent stem cells" means stem cells capable of differentiating into three-germ-layer cells (endoderm, mesoderm and ectoderm) (pluripotency), and is preferably intended to include not only embryonic stem cells, but also cells having this capability, among induced pluripotent stem (iPS) cells and adult stem cells.

In the present invention, endodermal cells that differentiated from stem cell-derived embryoid bodies can differentiate into the stomach, the colon, the liver, the spleen, the lungs, the airway epidermis, the larynx, the pharynx, the bladder, the urethral canal, the thyroid gland, the parathyroid, or the like. Each type of the cells may be produced by treating endodermal cells, which differentiated from the stem cell-derived embryoid bodies of the present invention, under specific differentiation conditions.

For example, differentiation into insulin-secreting pancreatic beta cells can be achieved by adding insulin to a medium during induction of the differentiation (Zalzman M et al., Proc Natl Acad Sci USA 100(12):7253-7258, 2003; Gao R et al., Diabetes 52, 2007-2015, 2003; Nakajima-Nagata N et al., Biochem Biophys Res Commun 318, 625-630, 2004; Hori Y et al., PLOS Med 2(4), e103, 2005.).

In the present invention, mesodermal cells that differentiated from stem cell-derived embryoid bodies can differentiate into muscles, skeletal muscles, connective tissue, cartilage, hard bone, skeleton, the genitourinary system, the kidneys, the spleen, the heart, adipose, blood, or the like. In addition, the cells can be produced by additionally treating mesodermal cells, which differentiated from the stem cell-derived embryoid bodies of the present invention, under specific differentiation conditions. For example, methods for producing the cells include a method of inducing differentiation into endothelial cells by culture in a medium containing VEGF, bFGF, IGF (insulin-like growth factor) and EGF (epidermal growth factor) (International Patent Publication WO 03/040319), a method of producing a hematopoietic lineage by culture in an environment comprising a hematopoietic growth factor selected from among SCF (stem cell factor), FLT-3 ligand, IL-3, IL-6 and G-CSF (granulocyte colony stimulating factor) (US Patent Publication No. US 2003/0153082), and the like.

Because the most time-consuming step in studies on stem cell differentiation is a step of analyzing the effect of a specific culture condition on the induction of differentiation, an effective method capable of inducing stem cells to differentiate into any germ layer is required. Particularly, in order to increase the utility of stem cells as a cell therapeutic agent by excluding the risk of contamination with other substances due to the use of differentiation inducers or the like, a technique of efficiently inducing stem cells to differentiate into specific cells is required.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1

Inhibition of CXCR2 Gene Expression in Human Pluripotent Stem Cells

Human pluripotent stem cells are able to differentiate into all types of human cells, but a significant portion about the induction of lineage-specific differentiation is still required to be developed. The present inventors have found that the cell membrane receptor CXCR2 plays an important role in the induction of lineage-specific differentiation of human pluripotent stem cells. Furthermore, the present inventors could induce selective differentiation by controlling the receptor CXCR2.

In this Example, in order to inhibit CXCR2 gene expression to thereby induce differentiation into endoderm and mesoderm, RNA interference that is a genetic manipulation technique was used to inhibit protein synthesis and gene function. In this technique, when a short hairpin RNA (shRNA) is introduced into cells using a vector, it binds to an mRNA having a sequence complementary to a portion of a target gene and cleaves the mRNA, thereby silencing the gene.

Specifically, human pluripotent stem cells (hPSCs, HI, iPSC) purchased from WiCell were cultured in a 24-well plate, and then infected for 18-20 hours with 10 μl of $1 \times 10^6$ TU/ml of shCXCR2 lentiviral particles (sc-40028-V, Santa Cruz Biotechnology, USA) added to 6 μg/ml of polybrane. The shCXCR2 lentiviral particles were composed of a pool of three different shRNA plasmids (sc-40028-VA, sc-40028-VB and sc-40028-VC, Santa Cruz Biotechnology, USA) comprising sequences of SEQ ID NOS: 1 to 3. On the next day, the medium was replaced, and then second infection was performed using the virus at a dose two-fold higher than that in the first infection. From 4-5 days to 8-10 days after the first viral infection, non-infected cells were removed by treatment with 1 μg/ml of puromycin.

Example 2

Inhibition of CXCR2 Gene Expression and Examination of Differentiation Capability After inhibition of CXCR2 gene expression, the expression of human pluripotent stem cell marker genes (OCT4, SOX2, and SSEA-4) was analyzed by immunofluorescence staining and real-time quantitative PCR.

Specifically, cells were fixed with 4% formaldehyde solution for 10 minutes, permeabilized with 0.1% Triton X-100, and blocked with 0.3% serum solution. Then, the cells were incubated overnight with a 1:1000-2000 dilution of primary antibody (Cell Signaling Technology, Inc., USA) for stem cell marker genes (OCT4, SOX2 and SSEA-4) at 4° C. On the next day, the primary antibody was washed out with 1×PBS solution, after which the cells were incubated with fluorescent dye-conjugated secondary antibody at room temperature for 2 hours, and then mounted on a cover glass and observed using a fluorescence microscope (Olympus).

In addition, using a Qiagen RNeasy kit (Qiagen Hilden, Germany), RNAs were isolated from the cells in which CXCR2 gene expression was inhibited. cDNAs were synthesized using 2 μg of each of the isolated RNAs, oligo(dT) and Superscript II reverse transcriptase (Gibco). Primers for stem cell marker genes (OCT4, SOX2 and SSEA-4) and an iQ SYBR Green qPCR Master Mix were added to each of the synthesized cDNAs, and analysis was performed using a Bio-Rad iCycler iQ system (Bio-Rad Laboratories, USA). The analysis results were normalized using the GAPDH gene, and P values were used to determine statistical significance (*$P<0.05$, $P<0.01$, and *$P<0.001$).

The primers used to analyze the expression of stem cell marker genes are as follows:

CXCR2: CAATGAATGAATGAATGGCTAAG (SEQ ID NO: 4)/AAAGTTTTCAAGGTTCGTCCGTGTT (SEQ ID NO: 5)

OCT4: TCTCGCCCCCTCCAGGT (SEQ ID NO: 6)/GCCCCACTCCAACCTGG (SEQ ID NO: 7)

NANOG: AAAGAATCTTCACCTATGCC (SEQ ID NO: 8)/GAAGGAAGAGGAGAGACAGT (SEQ ID NO: 9)

REX1: CAGATCCTAAACAGCTCGCAGAAT (SEQ ID NO: 10)/GCGTACGCAAATTAAAGTCCAGA (SEQ ID NO: 11)

GAPDH: GAGTCCACTGGCGTCTTCAC (SEQ ID NO: 12)/TTCACACCCATGACGAACAT (SEQ ID NO: 13)

As a result, it could be seen that the expression of stem cell marker genes (OCT4, SOX2, and SSEA-4) in the human pluripotent stem cells in which CXCR2 gene expression was inhibited was significantly reduced compared to that in control cells (FIGS. 1B and 2). In other words, it could be seen that, when the expression of the receptor CXCR2 in the human pluripotent stem cells maintained in an undifferentiated state was inhibited by the shRNA technique, the stem cells would have the ability to differentiate.

Example 3

Analysis of Proliferation of Human Pluripotent Stem Cells

After inhibition of CXCR2 gene expression in human pluripotent stem cells, the proliferation of the cells was analyzed. Specifically, human pluripotent stem cells were seeded in a 96-well plate at a density of $1 \times 10^4$ cells/well, and then analyzed from 48 hours to 144 hours. 10 μl of CCK-8 (Dojindo Laboratories; Kumamoto, Japan) solution was added to the cells at the predetermined time points (48, 72, 96, 120 and 144 hrs), and then incubated for 3 hours, and the absorbance at 450 nm was measured.

As a result, it could be seen that the proliferation of the human pluripotent stem cells in which CXCR2 gene expression was inhibited was significantly reduced compared to that of the control group (FIG. 1C).

Example 4

Analysis of Differentiation into Endoderm and Mesoderm by Real-Time Quantitative PCR After induction of differentiation into endoderm and mesoderm by inhibition of CXCR2 gene expression, changes in the expressions of endoderm-specific markers (AFP, GATA4, ZO1, SOX17 and CXCR4 genes) and mesoderm-specific markers (T, Snail2, Myocardin, twist1 and mixl1 genes) were analyzed by real-time quantitative PCR.

Specifically, RNAs were isolated from differentiation-induced cells using a Qiagen RNeasy kit (Qiagen Hilden, Germany), and cDNAs were synthesized using 2 μg of each RNA, oligo(dT) and Superscript II reverse transcriptase (Gibco). Target gene primers and an iQ SYBR Green qPCR Master Mix were added to each of the synthesized cDNAs, and analysis was performed using a Bio-Rad iCycler iQ system (Bio-Rad Laboratories, USA). The results were normalized using the GAPDH gene, and P values were used to determine statistical significance (*P<0.05, P<0.01, and *P<0.001).

Primers used to analyze the expression of ectodermal, endodermal and mesodermal genes are as follows:

(1) Ectoderm Gene

NESTIN: GCGTTGGAA CAGAGGTTGGA (SEQ ID NO: 14)/TGGGAGCAAAGATCCAAGAC (SEQ ID NO: 15)

SOX1: CACAACTCG GAG ATC AGCAA (SEQ ID NO: 16)/GGTACTTGTAATCCGGGTGC (SEQ ID NO: 17)

PAX6: CTGGCTAGCGAAAAGCAACAG (SEQ ID NO: 18)/CCCGTTCAACATCCTTAGTTTATCA (SEQ ID NO: 19)

PROX1: GCTCCAATATGCTGAAGACC (SEQ ID NO: 20)/ATCGTTGATGGCTTGACGTG (SEQ ID NO: 21)

(2) Mesoderm Gene

T(Brachyury): AATTGGTCC AGCCTTGGAAT (SEQ ID NO: 22)/CGTTGCTCACAGACCACA (SEQ ID NO: 23)

SNAIL2: ACAGCGAACTGGACACACAT (SEQ ID NO: 24)/GATGGGGCTGTATGCTCCT (SEQ ID NO: 25)

MIXL1: GGTACCCCGACATCCACTT (SEQ ID NO: 26)/GCCTGTTCTGGAACCATACCT (SEQ ID NO: 27)

TWIST1: AGCTACGCCTTCTCGGTCT (SEQ ID NO: 28)/CCTTCTCTGGAAACAATGACATC (SEQ ID NO: 29)

MYOCARDIN: TCACTTTCTGCCCTCATCCT (SEQ ID NO: 30)/TCGTGTGCTCCTGAGTTCTG (SEQ ID NO: 31)

Fltl: TCATGAATGTTTCCCTGCAA (SEQ ID NO: 32)/ GGAGGTATGGTGCTTCCTGA (SEQ ID NO: 33)

(3) Endoderm Gene

AFP: AGAACCTGTCACAAGCTGTG (SEQ ID NO: 34)/GACAGCAAGCTGAGGATGTC (SEQ ID NO: 35)

GATA4: TCCCTCTTCCCTCCTCAAAT (SEQ ID NO: 36)/TCAGCGTGTAAAGGCATCTG (SEQ ID NO: 37)

CXCR4: CCTGCCTGGTATTGTCATCC (SEQ ID NO: 38)/AGGATGACTGTGGTCTTGAGG (SEQ ID NO: 39)

ZO1: GGTCAGAGCCTTCTGATCATTC (SEQ ID NO: 40)/CATCTCTACTCCGGAGACTGC (SEQ ID NO: 41)

SOX17: CAGACTCCTGGGTTTTTGTTGTTGCTG (SEQ ID NO: 42)/GAAATGGAGGAAGCT-GTTTTGGGACAC (SEQ ID NO: 43)

Foxa2: TTCTCCATCAACAACCTCATGTCC (SEQ ID NO: 44)/GTAGTGCATCACCTGTTCGTAGG (SEQ ID NO: 45)

Figure 4:
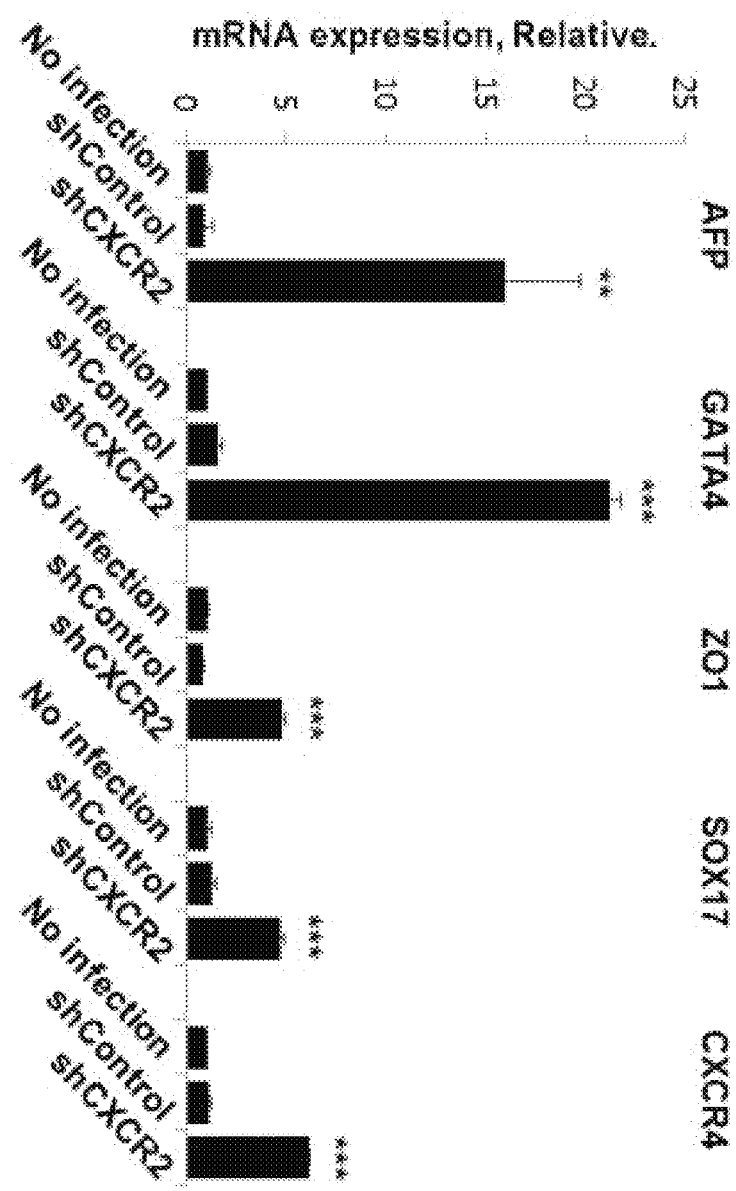
FIG. 4 shows the results of analyzing the expression of endodermal genes, including AFP, GATA4, ZO1, Sox17 and CXCR4, by real-time quantitative PCR.
Figure 5:
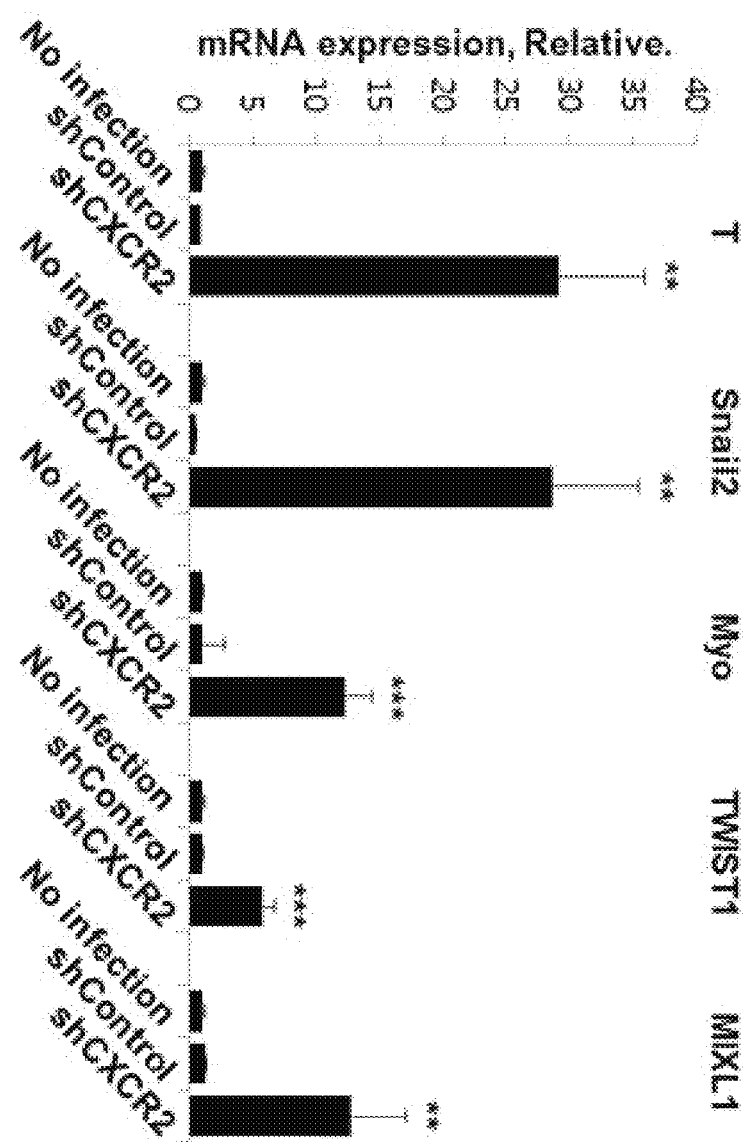
FIG. 5 shows the results of analyzing the expression of mesodermal genes, including T, Snail2, Myocardin, Twist1 and Mixl1, by real-time quantitative PCR.

As a result, it was shown that the expressions of endoderm-specific markers (AFP, GATA4, ZO1, SOX17 and CXCR4 genes) and mesoderm-specific markers (T, Snail2, Myocardin, twist1 and mixl1 genes) in the CXCR2 gene-silenced human pluripotent stem cells were significantly higher than those in the control cells (FIGS. 4 and 5). Such results appeared to be identical under all the conditions regardless of the difference in the composition of the medium.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

---

The invention claimed is:

1. A method for inducing the differentiation of pluripotent stem cells into endoderm or mesoderm, the method comprising a step of either in vitro treating the pluripotent stem cells with a CXCR2 expression inhibitor or culturing the pluripotent stem cells in a medium containing a CXCR2 antagonist.

2. The method of claim 1, wherein the CXCR2 expression inhibitor is an shRNA specific for CXCR2 mRNA.

3. The method of claim 2, wherein the shRNA is selected from the group consisting of SEQ ID NOS: 1 to 3.

4. The method of claim 1, wherein the CXCR2 antagonist is SB225002 or SB265610.

5. The method of claim 1, wherein the endoderm expresses one or more genes selected from the group consisting of AFP, GATA4, ZO1, SOX17, and CXCR4.

6. The method of claim 1, wherein the mesoderm expresses one or more genes selected from the group consisting of T, Snail2, Myocardin, twist1, and mixl1.

7. The method of claim 1, wherein the pluripotent stem cells are human embryonic stem cells or human induced pluripotent stem (iPS) cells.

* * * * *

SEQUENCE LISTING

```
<160> NUMBER OF SEQ ID NOS: 45

<210> SEQ ID NO 1
<211> LENGTH: 47
<212> TYPE: DNA
<213> ORGANISM: Artificial Sequence
<220> FEATURE:
<223> OTHER INFORMATION: shRNA-1

<400> SEQUENCE: 1
gtctactcat ccaatgttat tcaagagata acattggatg agtagac          47

<210> SEQ ID NO 2
<211> LENGTH: 47
<212> TYPE: DNA
<213> ORGANISM: Artificial Sequence
<220> FEATURE:
<223> OTHER INFORMATION: shRNA-2

<400> SEQUENCE: 2
cctcaagatt ctagctatat tcaagagata tagctagaat cttgagg          47

<210> SEQ ID NO 3
<211> LENGTH: 47
<212> TYPE: DNA
<213> ORGANISM: Artificial Sequence
<220> FEATURE:
<223> OTHER INFORMATION: shRNA-3

<400> SEQUENCE: 3
gccactaaat tgacacttat tcaagagata agtgtcaatt tagtggc          47
```

```
<210> SEQ ID NO 4
<211> LENGTH: 23
<212> TYPE: DNA
<213> ORGANISM: Artificial Sequence
<220> FEATURE:
<223> OTHER INFORMATION: CXCR2-F

<400> SEQUENCE: 4
caatgaatga atgaatggct aag                                              23

<210> SEQ ID NO 5
<211> LENGTH: 25
<212> TYPE: DNA
<213> ORGANISM: Artificial Sequence
<220> FEATURE:
<223> OTHER INFORMATION: CXCR2-R

<400> SEQUENCE: 5
aaagttttca aggttcgtcc gtgtt                                            25

<210> SEQ ID NO 6
<211> LENGTH: 17
<212> TYPE: DNA
<213> ORGANISM: Artificial Sequence
<220> FEATURE:
<223> OTHER INFORMATION: OCT4-F

<400> SEQUENCE: 6
tctcgccccc tccaggt                                                     17

<210> SEQ ID NO 7
<211> LENGTH: 17
<212> TYPE: DNA
<213> ORGANISM: Artificial Sequence
<220> FEATURE:
<223> OTHER INFORMATION: OCT4-R

<400> SEQUENCE: 7
gccccactcc aacctgg                                                     17

<210> SEQ ID NO 8
<211> LENGTH: 20
<212> TYPE: DNA
<213> ORGANISM: Artificial Sequence
<220> FEATURE:
<223> OTHER INFORMATION: NANOG-F

<400> SEQUENCE: 8
aaagaatctt cacctatgcc                                                  20

<210> SEQ ID NO 9
<211> LENGTH: 20
<212> TYPE: DNA
<213> ORGANISM: Artificial Sequence
<220> FEATURE:
<223> OTHER INFORMATION: NANOG-R

<400> SEQUENCE: 9
gaaggaagag gagagacagt                                                  20

<210> SEQ ID NO 10
<211> LENGTH: 24
<212> TYPE: DNA
<213> ORGANISM: Artificial Sequence
<220> FEATURE:
<223> OTHER INFORMATION: REX1-F
```

-continued

```
<400> SEQUENCE: 10
cagatcctaa acagctcgca gaat                                            24

<210> SEQ ID NO 11
<211> LENGTH: 23
<212> TYPE: DNA
<213> ORGANISM: Artificial Sequence
<220> FEATURE:
<223> OTHER INFORMATION: REX1-R

<400> SEQUENCE: 11
gcgtacgcaa attaaagtcc aga                                             23

<210> SEQ ID NO 12
<211> LENGTH: 20
<212> TYPE: DNA
<213> ORGANISM: Artificial Sequence
<220> FEATURE:
<223> OTHER INFORMATION: GAPDH-F

<400> SEQUENCE: 12
gagtccactg gcgtcttcac                                                 20

<210> SEQ ID NO 13
<211> LENGTH: 20
<212> TYPE: DNA
<213> ORGANISM: Artificial Sequence
<220> FEATURE:
<223> OTHER INFORMATION: GAPDH-R

<400> SEQUENCE: 13
ttcacaccca tgacgaacat                                                 20

<210> SEQ ID NO 14
<211> LENGTH: 20
<212> TYPE: DNA
<213> ORGANISM: Artificial Sequence
<220> FEATURE:
<223> OTHER INFORMATION: NESTIN-F

<400> SEQUENCE: 14
gcgttggaac agaggttgga                                                 20

<210> SEQ ID NO 15
<211> LENGTH: 20
<212> TYPE: DNA
<213> ORGANISM: Artificial Sequence
<220> FEATURE:
<223> OTHER INFORMATION: NESTIN-R

<400> SEQUENCE: 15
tgggagcaaa gatccaagac                                                 20

<210> SEQ ID NO 16
<211> LENGTH: 20
<212> TYPE: DNA
<213> ORGANISM: Artificial Sequence
<220> FEATURE:
<223> OTHER INFORMATION: SOX1-F

<400> SEQUENCE: 16
cacaactcgg agatcagcaa                                                 20

<210> SEQ ID NO 17
```

```
<211> LENGTH: 20
<212> TYPE: DNA
<213> ORGANISM: Artificial Sequence
<220> FEATURE:
<223> OTHER INFORMATION: SOX1-R

<400> SEQUENCE: 17
ggtacttgta atccgggtgc                                            20

<210> SEQ ID NO 18
<211> LENGTH: 21
<212> TYPE: DNA
<213> ORGANISM: Artificial Sequence
<220> FEATURE:
<223> OTHER INFORMATION: PAX6-F

<400> SEQUENCE: 18
ctggctagcg aaaagcaaca g                                          21

<210> SEQ ID NO 19
<211> LENGTH: 25
<212> TYPE: DNA
<213> ORGANISM: Artificial Sequence
<220> FEATURE:
<223> OTHER INFORMATION: PAX6-R

<400> SEQUENCE: 19
cccgttcaac atccttagtt tatca                                      25

<210> SEQ ID NO 20
<211> LENGTH: 20
<212> TYPE: DNA
<213> ORGANISM: Artificial Sequence
<220> FEATURE:
<223> OTHER INFORMATION: PROX1-F

<400> SEQUENCE: 20
gctccaatat gctgaagacc                                            20

<210> SEQ ID NO 21
<211> LENGTH: 20
<212> TYPE: DNA
<213> ORGANISM: Artificial Sequence
<220> FEATURE:
<223> OTHER INFORMATION: PROX1-R

<400> SEQUENCE: 21
atcgttgatg gcttgacgtg                                            20

<210> SEQ ID NO 22
<211> LENGTH: 20
<212> TYPE: DNA
<213> ORGANISM: Artificial Sequence
<220> FEATURE:
<223> OTHER INFORMATION: T-F

<400> SEQUENCE: 22
aattggtcca gccttggaat                                            20

<210> SEQ ID NO 23
<211> LENGTH: 18
<212> TYPE: DNA
<213> ORGANISM: Artificial Sequence
<220> FEATURE:
<223> OTHER INFORMATION: T-R

<400> SEQUENCE: 23
```

-continued

```
cgttgctcac agaccaca                                          18

<210> SEQ ID NO 24
<211> LENGTH: 20
<212> TYPE: DNA
<213> ORGANISM: Artificial Sequence
<220> FEATURE:
<223> OTHER INFORMATION: SNAIL2-F

<400> SEQUENCE: 24
acagcgaact ggacacacat                                        20

<210> SEQ ID NO 25
<211> LENGTH: 19
<212> TYPE: DNA
<213> ORGANISM: Artificial Sequence
<220> FEATURE:
<223> OTHER INFORMATION: SNAIL2-R

<400> SEQUENCE: 25
gatggggctg tatgctcct                                         19

<210> SEQ ID NO 26
<211> LENGTH: 19
<212> TYPE: DNA
<213> ORGANISM: Artificial Sequence
<220> FEATURE:
<223> OTHER INFORMATION: MIXL1-F

<400> SEQUENCE: 26
ggtaccccga catccactt                                         19

<210> SEQ ID NO 27
<211> LENGTH: 21
<212> TYPE: DNA
<213> ORGANISM: Artificial Sequence
<220> FEATURE:
<223> OTHER INFORMATION: MIXL1-R

<400> SEQUENCE: 27
gcctgttctg gaaccatacc t                                      21

<210> SEQ ID NO 28
<211> LENGTH: 19
<212> TYPE: DNA
<213> ORGANISM: Artificial Sequence
<220> FEATURE:
<223> OTHER INFORMATION: TWIST1-F

<400> SEQUENCE: 28
agctacgcct tctcggtct                                         19

<210> SEQ ID NO 29
<211> LENGTH: 23
<212> TYPE: DNA
<213> ORGANISM: Artificial Sequence
<220> FEATURE:
<223> OTHER INFORMATION: TWIST1-R

<400> SEQUENCE: 29
ccttctctgg aaacaatgac atc                                    23

<210> SEQ ID NO 30
<211> LENGTH: 20
<212> TYPE: DNA
```

```
<213> ORGANISM: Artificial Sequence
<220> FEATURE:
<223> OTHER INFORMATION: MYOCARDIN-F

<400> SEQUENCE: 30
tcactttctg ccctcatcct                                                 20

<210> SEQ ID NO 31
<211> LENGTH: 20
<212> TYPE: DNA
<213> ORGANISM: Artificial Sequence
<220> FEATURE:
<223> OTHER INFORMATION: MYOCARDIN-R

<400> SEQUENCE: 31
tcgtgtgctc ctgagttctg                                                 20

<210> SEQ ID NO 32
<211> LENGTH: 20
<212> TYPE: DNA
<213> ORGANISM: Artificial Sequence
<220> FEATURE:
<223> OTHER INFORMATION: Flt1-F

<400> SEQUENCE: 32
tcatgaatgt ttccctgcaa                                                 20

<210> SEQ ID NO 33
<211> LENGTH: 20
<212> TYPE: DNA
<213> ORGANISM: Artificial Sequence
<220> FEATURE:
<223> OTHER INFORMATION: Flt1-R

<400> SEQUENCE: 33
ggaggtatgg tgcttcctga                                                 20

<210> SEQ ID NO 34
<211> LENGTH: 20
<212> TYPE: DNA
<213> ORGANISM: Artificial Sequence
<220> FEATURE:
<223> OTHER INFORMATION: AFP-F

<400> SEQUENCE: 34
agaacctgtc acaagctgtg                                                 20

<210> SEQ ID NO 35
<211> LENGTH: 20
<212> TYPE: DNA
<213> ORGANISM: Artificial Sequence
<220> FEATURE:
<223> OTHER INFORMATION: AFP-R

<400> SEQUENCE: 35
gacagcaagc tgaggatgtc                                                 20

<210> SEQ ID NO 36
<211> LENGTH: 20
<212> TYPE: DNA
<213> ORGANISM: Artificial Sequence
<220> FEATURE:
<223> OTHER INFORMATION: GATA4-F

<400> SEQUENCE: 36
tccctcttcc ctcctcaaat                                                 20
```

<210> SEQ ID NO 37
<211> LENGTH: 20
<212> TYPE: DNA
<213> ORGANISM: Artificial Sequence
<220> FEATURE:
<223> OTHER INFORMATION: GATA4-R

<400> SEQUENCE: 37
tcagcgtgta aaggcatctg                                               20

<210> SEQ ID NO 38
<211> LENGTH: 20
<212> TYPE: DNA
<213> ORGANISM: Artificial Sequence
<220> FEATURE:
<223> OTHER INFORMATION: CXCR4-F

<400> SEQUENCE: 38
cctgcctggt attgtcatcc                                               20

<210> SEQ ID NO 39
<211> LENGTH: 21
<212> TYPE: DNA
<213> ORGANISM: Artificial Sequence
<220> FEATURE:
<223> OTHER INFORMATION: CXCR4-R

<400> SEQUENCE: 39
aggatgactg tggtcttgag g                                             21

<210> SEQ ID NO 40
<211> LENGTH: 22
<212> TYPE: DNA
<213> ORGANISM: Artificial Sequence
<220> FEATURE:
<223> OTHER INFORMATION: ZO1-F

<400> SEQUENCE: 40
ggtcagagcc ttctgatcat tc                                            22

<210> SEQ ID NO 41
<211> LENGTH: 21
<212> TYPE: DNA
<213> ORGANISM: Artificial Sequence
<220> FEATURE:
<223> OTHER INFORMATION: ZO1-R

<400> SEQUENCE: 41
catctctact ccggagactg c                                             21

<210> SEQ ID NO 42
<211> LENGTH: 27
<212> TYPE: DNA
<213> ORGANISM: Artificial Sequence
<220> FEATURE:
<223> OTHER INFORMATION: SOX17-F

<400> SEQUENCE: 42
cagactcctg ggtttttgtt gttgctg                                       27

<210> SEQ ID NO 43
<211> LENGTH: 27
<212> TYPE: DNA
<213> ORGANISM: Artificial Sequence
<220> FEATURE:

```
<223> OTHER INFORMATION: SOX17-R

<400> SEQUENCE: 43
gaaatggagg aagctgtttt gggacac                                    27

<210> SEQ ID NO 44
<211> LENGTH: 24
<212> TYPE: DNA
<213> ORGANISM: Artificial Sequence
<220> FEATURE:
<223> OTHER INFORMATION: Foxa2-F

<400> SEQUENCE: 44
ttctccatca acaacctcat gtcc                                       24

<210> SEQ ID NO 45
<211> LENGTH: 23
<212> TYPE: DNA
<213> ORGANISM: Artificial Sequence
<220> FEATURE:
<223> OTHER INFORMATION: Foxa2-R

<400> SEQUENCE: 45
gtagtgcatc acctgttcgt agg                                        23
```